US00PP21457P2

(12) United States Plant Patent
Pieters

(10) Patent No.: US PP21,457 P2
(45) Date of Patent: Nov. 9, 2010

(54) ***CHRYSANTHEMUM* PLANT NAMED 'PPP UNY 09'**

(50) Latin Name: *Chrysanthemum morifolium*
Varietal Denomination: PPP UNY 09

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 0 days.

(21) Appl. No.: 12/462,579

(22) Filed: Aug. 5, 2009

(51) Int. Cl.
*A01H 5/00* (2006.01)

(52) U.S. Cl. ..... Plt./295
(58) Field of Classification Search ..... Plt./295

See application file for complete search history.

*Primary Examiner*—Annette H. Para
*Assistant Examiner*—Louanne C Krawczewicz Myers
(74) *Attorney, Agent, or Firm*—Mark P. Bourgeois

(57) ABSTRACT

A new and distinct *Chrysanthemum* plant cultivar is disclosed, characterized by small daisy type inflorescences, consistent flowering response to short days, blooming consistently after 49 days of short day length, yellow ray florets, free branching habit, and a consistent natural season flowering habit during the third week of September.

1 Drawing Sheet

Latin name of the genus and species: *Chrysanthemum morifolium.*

Variety denomination: 'PPP UNY 09'.

BACKGROUND OF THE INVENTION

The new cultivar 'PPP UNY 09' is a product of a cross between the male parent 'Yellow Urano' (U.S. Plant Pat. No. 13,101) and the female parent 'GEM ONE OST' (U.S. Plant Pat. No. 13,868). The new cultivar was discovered and selected by Dirk Pieters in October of 2000 in a greenhouse in Oostnieuwkerke, Belgium.

Asexual reproduction of the new cultivar 'PPP UNY 09' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP UNY 09' has not been observed under all possible environmental conditions. The phenotype may vary somewhat with variations in environment such as temperature, daylength, and light intensity, without, however, any variance in genotype. The following traits have been repeatedly observed and are determined to be the unique characteristics of 'PPP UNY 09.' These characteristics in combination distinguish 'PPP UNY 09' as a new and distinct *Chrysanthemum* cultivar:

1. Small, yellow, daisy-type inflorescences;
2. Consistent natural season flowering habit during the third week of September;
3. Free branching habit; and
4. Consistent flowering response to short days, blooming consistently after 49 days of short day length.

Plants of the new cultivar 'PPP UNY 09' are similar to plants of the male parent variety, 'Yellow Urano' in most horticultural characteristics, however plants of the new cultivar 'PPP UNY 09' have a more solid daisy inflorescence form compared to the decorative inflorescence of 'Yellow Urano', which opens to a multiplex daisy. Also, the new cultivar 'PPP UNY 09' has a smaller inflorescence diameter and longer inflorescence longevity. Additionally, the ray florets of 'PPP UNY 09' are a different color yellow than the male parent. Finally, 'PPP UNY 09' naturally blooms two to three weeks later than the male parent 'Yellow Urano'.

Plants of the new cultivar 'PPP UNY 09' are similar to plants of the female parent variety, 'GEDI ONE OST' in most horticultural characteristics, however plants of the new cultivar 'PPP UNY 09' are shorter but have a wider plant spread. Also, the new cultivar 'PPP UNY 09' has a smaller inflorescence diameter. Additionally, the ray florets of 'PPP UNY 09' are a different color yellow than the female parent. Finally, 'PPP UNY 09' naturally blooms one week earlier than the female parent.

In comparison to the commercially available variety 'GEDI YP' (U.S. Plant Pat. No. 11,238), 'PPP UNY 09' is shorter and wider. Additionally, the new variety 'PPP UNY 09' has a larger inflorescence diameter and lighter yellow ray florets. Further, the new variety 'PPP UNY 09' has more ray florets per inflorescence. Finally, 'PPP UNY 09' blooms one week earlier than the comparable variety.

BRIEF DESCRIPTION OF THE PHOTOGRAPH

The accompanying photograph in the drawing illustrates in full color a typical plant of 'PPP UNY 09' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP UNY 09' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* 'PPP UNY 09'.
Commercial classification: Garden-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 17 cm.
Plant spread: Approximately 30 cm.
Growth rate: Moderate.
Branching characteristics: Free Branching.
Length of lateral branches: Approximately 13 cm.
*Diameter of lateral branches.*—About 4.7 mm.
*Color of lateral branches.*—Near Green 137A.
Number of leaves per lateral branch: Approximately 25.
Age of plant described: Approximately 137 days.

FOLIAGE

Leaf:
*Arrangement.*—Alternate single.
*Average length.*—Approximately 4.1 cm.
*Average width.*—Approximately 3.7 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 1.1 cm.
*Color.*—Young foliage upper side: Near Green 137A. Young foliage under side: Near Green 138A. Mature foliage upper side: Near Green 137B. Mature foliage under side: Near Green 138B.
*Venation.*—Type: Palmately net. Venation color upper side: Near Green 138B. Venation color under side: Near Green 138C.
Petiole:
*Average length.*—Approximately 2.3 cm.
*Color.*—Near Green 138B.
*Diameter.*—Approximately0.2 cm.

BLOOM

Inflorescence:
*Flowering habit.*—Induced by darkness period greater than 13.5 hours, approximately 49 days of appropriate day length required to induce and develop blooms.
*Inflorescence form.*—Daisy.
*Natural flowering season.*—Approximately the third week in September.
*Number of inflorescences per lateral branch.*—Approximately 9.
*Inflorescence diameter.*—Approximately 3.2 cm.
*Inflorescence depth.*—Approximately 1.3 cm.
*Disc diameter.*—Approximately 1.2 cm.
*Receptacle height.*—About 6 mm.
*Receptacle diameter.*—About 4 mm.
*Fragrance.*—None.
*Inflorescence longevity on plant.*—Approximately 28 to 34 days.
*Persistence.*—Persistent.
Ray florets:
*Appearance.*—Matte.
*Texture* (*both surface*).—Smooth.
*Average number of ray florets per inflorescence.*—105.
*Shape.*—Oblanceolate.
*Aspect.*—Flat.
*Margin.*—Entire.
*Apex.*—Obtuse.
*Base.*—Attenuate.
*Length.*—Approximately 0.5 cm.
*Width:.*—Approximately 0.3 cm.
*Color.*—Upper surface at first opening: Near Yellow 4A. Upper surface at maturity: Near Yellow 4B. Upper surface at fading: Near Yellow 4C. Under surface at first opening: Near Yellow 4A. Under surface at maturity: Near Yellow 4B. Under surface at fading: Near Yellow 4C.
Disc florets:
*Appearance.*—Shiny.
*Texture.*—Smooth.
*Average number of florets per disc.*—Approximately 28.
*Shape.*—Cylindric.
*Apex.*—Obtuse.
*Average length.*—Approximately 0.2 cm.
*Average width.*—Approximately 0.1 cm.
*Color.*—At first opening: Near Yellow-Green 154C. At maturity: Near Yellow 12A. At fading: Near Yellow 12A.
Peduncle:
*Length.*—At terminal end (shortest): Approximately 4 cm. At lateral end (longest): Approximately 6 cm.
*Angle to stem.*—Acute.
*Strength.*—Moderate.
*Color.*—Near Green 138B.
*Habit.*—Upright.
*Diameter.*—Approximately 0.3 cm.
*Surface texture.*—Lightly pubescent.
Inflorescence bud:
*Length.*—Approximately 0.5 cm.
*Diameter.*—Approximately 0.5 cm.
*Form.*—Globose.
*Color.*—Near Yellow 12A.
Involucral bracts (phyllaries):
*Appearance.*—Matte.
*Texture.*—Lightly pubescent.
*Number.*—Approximately 25.
*Shape.*—Lanceolate.
*Margin.*—Entire.
*Apex.*—Obtuse.
*Length.*—Approximately 0.5 cm.
*Width.*—Approximately 0.3 cm.
*Color.*—Upper side: Near Green 137A. Under side: Near Green 137B.

REPRODUCTIVE ORGANS

Ray florets:
*Number of pistils per floret.*—1.
*Stigma shape.*—2 branched.
*Stigma color.*—Near Yellow 9A.
*Style color.*—Near Green-Yellow 1D.
*Style length.*—Approximately 0.3 cm.

*Stamens.*—Absent.

Disc florets:

*Number of pistils per floret.*—1.

*Stigma shape.*—Cylindric.

*Stigma color.*—Near Yellow 13A.

*Style length.*—Approximately 0.2 cm.

*Style color.*—Near Green-Yellow 1D.

*Number of stamens per floret.*—Approximately 5.

*Anther shape.*—Tubular.

*Anther color.*—Near Yellow 13A.

*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP UNY 09' as herein illustrated and described.

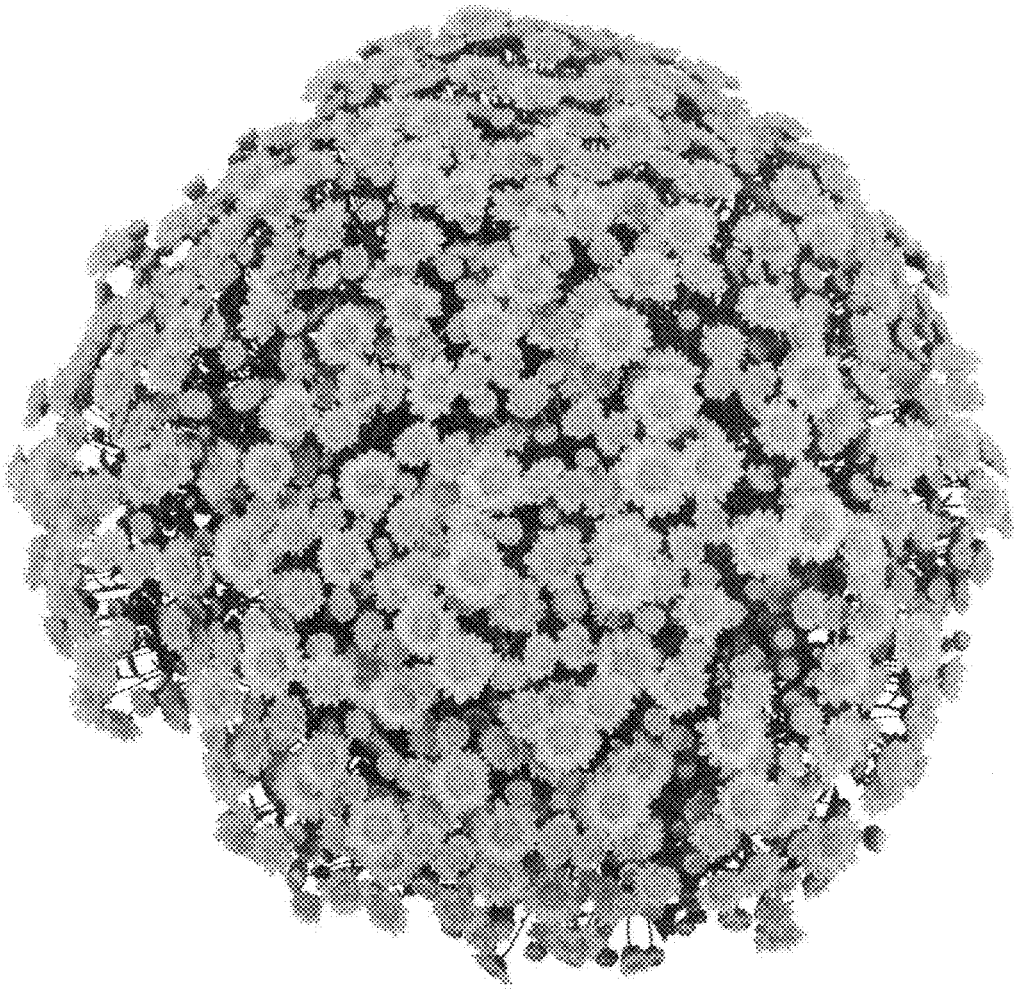

* * * * *